United States Patent [19]

Hazen et al.

[11] Patent Number: 5,084,087
[45] Date of Patent: Jan. 28, 1992

[54] READY TO DILUTE ADJUVANT-CONTAINING POSTEMERGENT HERBICIDE FORMULATIONS

[75] Inventors: James L. Hazen, Apex, N.C.; James R. Campbell, Lesotho, South Africa

[73] Assignee: BASF Corporation, Wyandotte, Mich.

[21] Appl. No.: 343,785

[22] Filed: Apr. 26, 1989

[51] Int. Cl.$^5$ ............... A01N 31/14; A01N 35/06
[52] U.S. Cl. ........................... 71/123; 71/88; 71/103; 71/124; 71/DIG. 1
[58] Field of Search ............ 71/103, DIG. 1, 124, 71/123, 88

[56] References Cited

U.S. PATENT DOCUMENTS

| | | | |
|---|---|---|---|
| 4,249,937 | 2/1981 | Iwataki et al. | 71/103 |
| 4,447,257 | 5/1984 | Gerwick, III | 71/DIG. 1 |
| 4,834,908 | 5/1989 | Hazen et al. | 252/236 |

FOREIGN PATENT DOCUMENTS 6810762  2/1970  Netherlands ............... 71/DIG. 1

OTHER PUBLICATIONS

McCowan, "Turf Herbicide Rx: Add Oil", *Agricult. Chem.* (23)4, Apr. 1968.
Thomson, *Agricultural Chemicals, Book II Herbicides* (1983–1984 Revision), 1983, Thomson Publications, pp. 238–239.
*References in Ser. No. 358,324 and Ser. No. 323,771.

*Primary Examiner*—Richard L. Raymond
*Assistant Examiner*—Brian M. Burn

[57] ABSTRACT

Ready-to-Dilute (RTD) herbicide formulations containing crop oil type adjuvants are disclosed which may be added as is to water to form a tank mix for herbicide application. The formulations are storage stable for extended periods, provide for rapid self-emulsification, form a stable tank mix, and moreover provide equal or better herbicidal efficiency than tank mixes containing commercially available standard crop oils and standard herbicide formulations.

8 Claims, No Drawings

READY TO DILUTE ADJUVANT-CONTAINING POSTEMERGENT HERBICIDE FORMULATIONS

BACKGROUND OF THE INVENTION

1. Field of the Invention

The subject invention relates to adjuvants for postemergent herbicides, which fall into the category of crop oil concentrates. More particularly, the subject invention relates to improved crop oil concentrates which enhance the efficacy of herbicides, allowing greater or equal weed control while using less active ingredient, while being capable of being mixed with the herbicidal active ingredient to form a storage stable, self-emulsifying, ready-to-dilute (RTD) formulation.

2. Description of the Related Art

It is well established that a variety of adjuvants play important roles in the application of herbicides. These adjuvants are a diverse group of components with equally diverse functions which may often be determined from their generic names, i.e. "spreaders," "stickers," "solubilizers," "emulsifiers," "flow control agents," "drift control agents," and so on. Among the many useful herbicide adjuvants are the so-called "crop oil concentrates."

Crop oil concentrates are often recommended by herbicide manufacturers and formulators for inclusion in tank mixes to increase the efficacy of postemergent herbicide formulations. Crop oil concentrates are available from a variety of sources, and generally consist of from 75-95 percent by weight of a hydrocarbon oil or solvent with the balance being a surfactant, although in certain cases the surfactant may comprise a majority of the composition, or even all of the composition.

The hydrocarbons which form a major part of the crop oil concentrate may be derived from mineral (petroleum) or vegetable sources. When derived from mineral sources, the hydrocarbon component may be predominantly paraffinic, or may be aromatic, particularly alkylated aromatic.

Although the use of selected crop oil concentrates may enhance herbicidal efficacy, it is well known that many of the proprietary concentrates available are not as effective as others. Some may even impact negatively upon herbicidal efficacy. Additionally, there is a great deal of inconsistency with regard to the composition of available crop oil concentrates, complicated by the fact that manufacturers frequently change formulations without notifying the consumer, resulting in a great deal of uncertainty with regard to their performance.

In recent years herbicide/crop oil premixes have become commercially desirable products. Thus rather than having to prepare a tank mix from separate herbicide and crop oil containers, it would be desirable to prepare herbicides and crop oils in one formulation which is ready to dilute. Such RTD formulations present further problems. For example, the presence of active chemical species in the formulation may cause decomposition of the active ingredient, and thus the storage life of the formulation may be unduly limited. Moreover, the formulation must be freeze thaw stable, and should in addition be self-emulsifying when added to the application tank. Finally, the result emulsion or dispersion should be stable over at least a half hour to several hours under moderate agitation.

One commercial sethoxydim ready-to-dilute formulation, NABU-S, a product of Nippon Soda, utilizes polyoxyethylated fatty acid and a sorbitan fatty acid ester as emulsifiers in an amount of about 26 weight percent along with about 61.5 weight percent of machine oil. However, this formulation loses approximately 25 percent of its activity after only 3 months storage at 50° C., and is not particularly effective at enhancing sethoxydim activity.

In copending U.S. application Ser. No. 104,658 are disclosed crop oil concentrates which not only are highly effective with a broad spectrum of individual herbicides, but also unexpectedly decrease the apparent antagonism often exhibited when two or more herbicides are used together. These crop oils contain an aromatic or paraffinic solvent or diluent, a fatty acid, one or more lower alkyl fatty acid esters, and a particular group of anionic surfactants which are polyoxyalkylene sulfates, phosphates, or carboxylates. Unfortunately, this highly effective crop oil concentrate, when added to cyclohexenone herbicides to prepare a ready-to-dilute formulation, causes rapid degradation of the active ingredient, and thus its use must be restricted to tank mixes prepared from individual herbicides and crop oils.

Copending U.S. application Ser. No. 237,609 disclosed crop oil adjuvants which, while not especially effective in avoiding herbicide antagonism, nevertheless are very effective crop oils, especially with cyclohexenone herbicides. However, once again, when combined with the active herbicidal cyclohexenone in a ready-to-dilute formulation, considerable decomposition of the active ingredient occurs.

SUMMARY OF THE INVENTION

It has now been surprisingly discovered that certain crop oil concentrates enhance the activity of cyclohexenone herbicides over and above the efficacy obtained with many other, commercial adjuvants, and yet may be formulated into freeze-thaw stable, self-emulsifying, ready-to-dilute herbicide preparations which maintain the activity of the active ingredient for long periods of time.

DESCRIPTION OF THE PREFERRED EMBODIMENTS

The crop oil concentrates of the subject invention comprise a mixture of (a) one or more herbicides (b) an emulsifier component which is a combination of (i) a polyoxyalkylene nonionic surfactant having an HLB of from 10 to about 14, and (ii) an anionic surfactant selected from the group consisting of the dialkyl metal sulfosuccinates and the metal alkylbenzene sulfonates; (c) optionally a second surface active component which is a low foaming polyoxyalkylene nonionic surfactant having an HLB of less than 10; and (d) a lower alkanol ester of a long chain fatty acid. As an additional, optional component, a hydrocarbon "oil" may be added.

The amount of active herbicide (a) may vary, but is generally from 10 to about 250 g/L, preferably from 50 to about 150 g/L, and most preferably from 90 to abut 120 g/L. Higher amounts of herbicide may require more surfactant and may prove difficult to formulate, while amounts less than 30 g/L are, in general, uneconomically small.

The polyoxyalkylene nonionic surfactant (b)(i) has an HLB preferably from 10 to about 14, and more preferably about 12. Highly suitable, for example, are the polyoxyethylene ethers of fatty alcohol or alkylphenol hydrophobes. These polyoxyethylene ethers may contain from about 6 to about 20 ethylene oxide residues depending inversely upon the molecular weight of the hydrophobe. Polyoxyethylated fatty acids and amides having similar HLB values may also be useful but are not preferred due to greater likelihood of hydrolysis.

The preferred polyoxyalkylene nonionic surfactants are prepared by oxyethylating a fatty alcohol having from 10 to about 20 carbon atoms, for example decyl, tridecyl, lauryl, and stearyl alcohols, or an alkylphenol such as octyl, nonyl, or decylphenol with from 6 (for decyl or tridecyl) to about 15 ethylene oxide units. Most preferably, the polyoxyalkylene nonionic surfactant (b)(i) is a POE (8) nonyl or decylphenol.

The anionic surfactant (b)(ii) is an alkylsulfosuccinate salt or an alkylbenzenesulfonate salt, or mixture thereof. The alkysulfosuccinates are generally prepared by the esterification of maleic acid or maleic anhydride with from 1 to 2, preferably 2 moles of an aliphatic alcohol followed by the addition of sodium bisulfite, or other bisulfite salt. Preferably, the aliphatic alcohol contains from 4 to about 20 carbon atoms. Most preferably the alcohol is 2-ethylhexanol. The reaction product of maleic anhydride, 2-ethylhexanol, and sodium bisulfite is known in the trade as dioctylsodiumsulfosuccinate, and is the most preferred anionic surfactant.

Also suitable are the salts of the alkylbenzenesulfonates, particularly the 2-ethylhexylbenzenesulfonates, nonylbenzenesulfonates, decylbenzenesulfonates, and dodecylbenzenesulfonates. Most preferred are the calcium salts, although the alkali metal salts and other alkaline earth metal salts may also be used. Most preferred is calcium dodebylbenzenesulfonate. When the metal alkylbenzene sulfonates are utilized, it is particularly important that the water level in the overall composition be minimal, e.g. less than 100 ppm.

The nonionic surfactant (b)(i) and the anionic surfactant (b)(ii) are used in such amounts that component (b) contains from 95 to about 60 percent of nonionic surfactant (b)(i) and from 5 to about 40 percent anionic surfactant (b)(ii). Component (b) is present in the final ready-to-dilute herbicide formulation in an amount of from 5 to about 100 g/L, preferably from 10 to 50 g/L, and most preferably from 20–25 g/L.

The low foaming nonionic surfactant (c) is optional in the sense that acceptable formulations may be made without it, for example by replacing it with an aromatic or paraffinic solvent. However, and particularly the case with the cyclohexenone herbicides, the presence of component (c) appears to improve the formulation in three ways: 1) by improving the self-emulsifying properties of the formulation; 2) by improving the effectiveness of the herbicide as applied to the target weed species, and most unexpectedly, 3) by improving the storage stability of the active herbicide ingredient. The low foaming nonionic surfactant (c) is preferably used in concentration of from 10 to about 100 g/L, more preferably from 30 to about 70 g/L, and most preferably about 50 g/L.

The low foaming surfactants (c) are polyoxyalkylene nonionic surfactants initiated with long chain aliphatic alcohols which have little tendency to foam as measured, for example, by the Ross-Miles test. Preferably, the low foaming surfactant should have a dynamic foam height measured at 0.1 percent concentration and 50° C., of less than about 10 cm, more preferably less than 6 cm, and most preferably about 3 cm or less. The low foaming surfactants typically have hydrophile/lipophile (HLB) values of less than 10, preferably less than 8 and most preferably about 6 or less.

The low foaming surfactants (c) of the subject invention comprise two related types of surfactants of their mixtures. Both types of low foamers are initiated with long chain fatty alcohols having chain lengths of from 6 to 22, preferably from 10 to 18, and particularly from 13 to 15 carbons in the aliphatic hydrocarbon portion of the molecule.

One type of low foamer (c) is prepared by oxyethylating the previously described aliphatic alcohols with from 2–6 moles of ethylene oxide, preferably 3–5 moles. The second type of low foamer is prepared by oxyalkylating the aliphatic alcohol initiator with both ethylene oxide and a higher alkylene oxide, preferably propylene oxide, butylene oxide, or mixtures thereof. The oxyalkylation by the various alkylene oxides may take place substantially sequentially or may take place concurrently, the product having the low foaming properties previously described.

In this second type of low foaming surfactant, from 2 to about 20 moles of ethylene oxide and from 1 to about 15 moles of higher alkylene oxide are utilized. Preferably, the oxyalkylation is sequential and involves the addition of preferably from 2 to about 12, more preferably from 2 to about 10 moles of ethylene oxide followed by the addition of from 1 to about 15, preferably from 1 to about 10 moles of higher alkylene oxide. When butylene oxide is the higher alkylene oxide, generally less higher alkylene oxide need be used than when propylene oxide is the higher alkylene oxide. From 1 to about 4 moles of butylene oxide is preferred.

When both alkylene oxides are added concurrently to form a heteric low foaming surfactant, from 2 to about 18 moles, preferably 4 to about 8 moles of ethylene oxide are used with from 2 to about 10, preferably 3 to about 7 moles of higher alkylene oxide.

The lower alkanol ester of the long chain carboxylic acid (d) may be considered as derived from a lower alkanol having from 1 to 4 carbon atoms, such as methyl alcohol, ethyl alcohol, propyl alcohol, or butyl alcohol, and a long chain carboxylic acid. The methyl and ethyl esters are preferred. Most particularly, the methyl esters are utilized. The long chain carboxylic acid preferably contains from 6–22 carbon atoms, more preferably from 14–18 carbon atoms. Most preferred are those carboxylic acids obtainable from natural sources such as fats and oils, for example lauric, myristic, stearic, linoleic, linolenic, palmitic, and oleic acids. Unsaturated fatty acids are preferred over their saturated analogs. Mixtures of these acids are also useful. Preferred are oleic and palmitic acids and their mixtures. Thus the most preferred alkanol esters are methyl oleate, methyl palmitate, and mixtures of these esters. In the remainder of the specification, such compounds will be referred to as lower alkanol esters.

In order to improve the low temperature stability, it is desirable that a goodly portion of the lower alkanol ester comprise methyloleate or another alkanol ester with a low freezing point and/or high low temperature solubility in other system components. Unfortunately, the use of methyloleate along renders the formulation less bioactive then when the preferred mixtures of methyloleate and methylpalmitate are used. Thus the most preferred embodiment utilizes a mixture containing approximately 60 weight percent methyl oleate and approximately 40 weight percent of a commercially available mixture containing approximately 50 percent each of methyloleate and methylpalmitate. Of course other mixtures may be used, particularly where low temperature stability is not important, and other lower alkanol esters, particularly those of naturally occurring unsaturated fatty acids may provide yet better formulations.

The lower alkanol ester or mixture of esters is generally used in an amount such that the finally ready-to-dilute formulation is made up to volume with the ester component. However, it may also be desirable to make up the volume by the addition of a paraffinic or aromatic solvent. In such cases, the lower alkanol ester should preferably comprise about 10 weight percent or more, or greater than about 100 g/L of the total ready-to-dilute system.

The optional hydrocarbon component may be derived principally from vegetable or petroleum sources. Preferred are the aromatic solvents, particularly those containing alkylated aromatics such as the benzenes and naphthalenes. All such solvents are readily available from a number of sources, for example, the Shellsolve ® solvents available from the Shell Oil Co., Houston, Tex., and the Aromatic ® 150 and 200 solvents available from the Exxon Corporation. The hydrocarbon component may also be a paraffinic "oil" or other non-aromatic solvent derived from mineral sources. Suitable paraffinic hydrocarbons are preferably solvent refined petroleum oil fractions composed of naphthenic as well as paraffinic hydrocarbons with less than about 25 weight percent of aromatics. Such hydrocarbon "oils" generally have high flashpoints, i.e. above 200° F., preferably about 300° F. Suitable, for example are the ISOPAR ® isoparaffinic solvents available from the Exxon Corporation. Mixtures of paraffinic aromatic hydrocarbons may also be used.

The optional hydrocarbon component may also contain up to about 30 percent by weight, preferably from 10–30 percent by weight of a solvent soluble alcohol, for example n-hexanol or isooctanol, to maintain or enhance the physical properties of the blend. Other solvent soluble alcohols which are suitable are those which generally contain from 5 to about 18 carbon atoms, preferably from 5 to about 10 carbon atoms. The term "hydrocarbon component" as used herein should be taken as including both aliphatic and aromatic solvents as well as their mixtures, including also the solvent soluble alcohol component described immediately above.

The ready-to-dilute formulation of the subject invention may be utilized in tank mixes for many post-emergent herbicide formulations, generally in amounts of from about 0.5 to about 8 L/ha, preferably from about 1 to about 3 L/ha. The RTD formulations of the subject invention may be used with a wide variety of herbicides and plant growth regulators. For example, the inventors have found excellent results with phenoxyphenoxy herbicides, with imadazolinone type herbicides, with pyridyloxyphenoxy herbicides, and with triketone plant growth regulators. In other cases, the concentrates may be used as experience dictates. The ready-to-dilute formulations are especially effective with the cyclohexenone-type herbicides.

The cyclohexenone herbicides with which the subject invention crop oil concentrates may be used are well known. Examples of their preparation and use may be found in U.S. Pat. Nos. 3,950,420; 4,011,256; 4,249,937, and 4,666,510. Specific mention may be made of certain of the more common cyclohexenones, including alloxydim, sethoxydim, cycloxydim, clethodim, and cloproxydim.

The diphenyl ether herbicides and their analogues are likewise well known. These herbicides are described, for example, in chapter 14 of Herbicides, P. C. Kearney et. al., published by Marcel Dekker, Inc., New York ® 1976. Many other classes of herbicides are also described in this two volume treatise. Also well known are the dipyridilium herbicides such as paraquat, diquat, and morfamquat.

In the examples which follow, herbicides or herbicide mixtures are tested for their efficacy against a variety of common weeds. In many cases, comparisons are made to similar tank mix compositions prepared from other, separate crop oil concentrate components. The "standard" crop oil concentrate used for comparison purposes is "Booster Plus E," a product of the Agway Corporation. This product has been widely used in herbicide applications and appears to have consistent formulation and product quality. In the examples, this "standard" crop oil concentrate is labeled "OC". In all the tables showing efficacy of the crop oil concentrate/herbicide mixtures against various species of weeds, the numerical values in the tables represent the percentage of weed control, or percent kill of the various species. The term "Concentrate" is used to represent "crop oil concentrate" in these tables. In other cases, the $GR_{50}$ and $GR_{80}$ values are cited. These latter are the concentrations required to provide 50 percent and 80 percent control of the weed species under consideration. Average GR values represent the average of the $GR_{50}$ and $GR_{80}$ values.

In comparing the efficacy of the subject invention crop oil concentrates with alternative crop oil concentrates, the respective concentrates were added at levels of generally from 1 to 5 L/ha to tank mixes of the herbicides and agitated to prepare a uniform mixture. The subject invention RTD formulation was merely added to the tank mix. The herbicide active concentrations were made equivalent.

Standard abbreviations for the various weed species found in the text which follows may be found below:

| ABUTH | Abuthilon theophrasi | velvet leaf |
|---|---|---|
| AVEFA | Avena fatua | wild oats |
| AVESA | Avena sativa | oats (volunteer) |
| BRAPP | Brachiaraia platyphylla | broadleaf signal grass |
| BROSE | Bromus secalinus | cheatgrass |
| CHEAL | Chenopodium album | common lambsquarter |
| CYNDA | Cynodon datylon | bermudagrass |
| DAOTA | Daubentonia texana | coffee weed |
| DATST | Datura stramonium | jimsonweed |
| DIGSA | Digitoria sanguinalis | large crabgrass |
| ECHCG | Echinochloa crus-galli | barnyardgrass |
| FESAR | Festuca arundinacea | tall fescue |
| HORVX | Hordeum vulgare | barley (volunteer) |
| IPOLA | Ipomoea lacunosa | pitted morning glory |
| IPOSS | Ipomoea spp. | morningglory species |
| LEFFI | Leptochloa filiformis | red sprangletop |
| LOLMU | Lolium multiflorum | annual ryegrass |
| PANTE | Panicum texanum | Texas panicum |
| POAAN | Poa annua | annual bluegrass |
| POAPR | Poa pratensus | Kentucky bluegrass |
| SETFA | Setaria faberii | giant fox tail |
| SETLU | Setaria lutescens | yellow foxtail |
| SETVI | Setaria viridis | green foxtail |
| SORHA | Sorghum halepense | Johnson grass |
| TRZAX | Triticum aestivum | wheat (volunteer) |
| TRFSS | Trifolium spp. | Clover species |
| XANPE | Xanthium pennsylvanicum | cocklebur |
| ZEAMD | Zea maydis | corn (dent) |

| | | |
|---|---|---|
| ZEAMX | *Zea mays* | corn (volunteer) |

Examples 1 and 2

RTD formulations were prepared from Sethoxydim technical (nominal 50% active in o-oxylene); an emulsifier (b) containing 80 weight percent of POE (8) nonylphenol and 20 weight percent dioctylsodiumsulfosuccinate; a low foaming surfactant PLURAFAC® LF 700 nonionic surfactant, a fatty alcohol initiated polyoxyethylenepolyoxypropylene block surfactant having a nominal molecular weight of 900 Daltons and available from BASF Corporation, Parsippany, N.J.; and sufficient alkanol ester to make the volume up to one liter. The alkanol ester utilized in RTD-1 is a 60:40 weight blend of Kemester® 104 (methyloleate) and Stepan C65, a commercial blend of methyl esters of higher fatty acids containing 36-52 weight percent of $C_{16}$ fatty acids and 45-60 percent of $C_{18}$ fatty acids, the esters consisting predominantly of the methyl esters of myristic, palmitic, oleic and stearic acids. For RTD-2, the methyl esters are KEMESTER® EX-714, a product of the Humko Div. of Witco Corporation, and comprising approximately 28 weight percent $C_{16}$ fatty acids and approximately 68 weight percent $C_{18}$ fatty acids, the majority of which are oleic acid. The remainder of the blend consists of minor amounts of the esters of other $C_{10}$-$C_{15}$ fatty acids. RTD-3 contains Stepan C65 as the methyl ester component. Following preparation of the above formulations, the water content is reduced to less than 1000 ppm. The formulations each comprised 120 g/L sethoxydim active (not technical), 25 g/L emulsifier, 50 g/L low foaming surfactant, with the greater part of the balance made up of the particular methyl ester mixture. Each also contained a minimal quantity (~120 g/L or less) of o-xylene or other solvent derived from the sethoxydim technical.

Tables I and II illustrate that the RTD formulation, despite containing slightly less adjuvant than otherwise similar tank mixes containing adjuvant in a quantity sufficient to provide adjuvant at a rate of 2 liters/ha, has equal or better performance than the standard concentrate when tested under field conditions in Soybeans and Broccoli.

TABLE I

Weed Control[1] by Sethoxydim in Soybeans at 150 g active/ha

| Formulation | Weed Species: | | | |
|---|---|---|---|---|
| | DIGSA | ZEAMX | ECHCG | Overall |
| Sethoxydim + OC @ 2 L/ha | 93 | 69 | 96 | 85 |
| RTD-1 | 92 | 70 | 95 | 84 |
| RTD-3 | 92 | 78 | 97 | 87 |

[1] percent weed control 7 days after test (DAT)

TABLE II

Weed Control by Sethoxydim in Broccoli at 150 g active/ha

| Formulation | Weed Species: | | | | |
|---|---|---|---|---|---|
| | ECHCG | BRAPP | LEFDU | SETFA | Overall |
| Sethoxydim + OC @ 2 L/ha | 100 | 100 | 57 | 100 | 89 |
| RTD-1 | 100 | 100 | 67 | 100 | 90 |
| RTD-3 | 100 | 100 | 53 | 100 | 88 |

TABLE III

Grass Control by Sethoxydim @ 27.2 g/A

| Formulation | % Grass Control[1] |
|---|---|
| Sethoxydim + 0.95 L/A OC | 49 |
| RTD-2 | 72 |

[1] Average of grass species tested.

TABLE IV

Burnout[1] of Rhizome Johnsongrass by Sethoxydim at 0.05 and 0.1 lbs/A

| Formulations | Rate: | |
|---|---|---|
| | 0.05 lbs/A | 0.1 lbs/A |
| Sethoxydim + 0.95 L/A OC | 29 | 84 |
| RTD-2 | 45 | 88 |

[1] expressed as percent control, greenhouse tests

The chemical stability of RTD formulations is of principle importance. Several formulations were tested for stability of the active ingredient over various time periods. The results are indicated in Table V below.

TABLE V

Formulated-Sethoxydim Storage Stability at 40° C. and 50° C., % active

| Formulation | 40° C. | 50° C. | Storage Time |
|---|---|---|---|
| DASH® | <50 | <50 | 3 months |
| RTD-C1 | 69 | 21 | 2 years |
| RTD-C2 | 39 | 7 | 2 years |
| RTD-4 | 70 | 30 | 2 years |
| RTD-3 | 85 | 47 | 2 years |
| RTD-2 | 90 | — | 3 months |
| RTD-1 | 97 | — | 3 months |
| NABU-S | — | 75 | 3 months |
| Sethoxydim + OC[4] | 75 | 36 | 3 months |

[1] DASH® adjuvant, a product of BASF Corporation falling within the scope of copending U.S. Ser. No. 104,658.
[2] RTD-C1 and RTD-C2 are comparative ready-to-dilute formulations containing the following components:
[2] Extrapolated value.
RTD-C1 60 g/L POE (4) lauryl alcohol; Stepan C65
RTD-C2 120 g/L Makon 8/Emulsifier (b) of subject invention; ISOPAR L
RTD-4: Emulsifier (b) of subject invention; C65 esters
[4] Sethoxydim technical diluted to volume with OC, and containing 15% active.

The table shows that the formulations of the subject invention have significant storage improvement over other formulations. The table also shows the surprising increase in stability (RTD-4 v. RTD-3) when the low foaming surfactant is added to the formulation.

The subject invention RTD formulations are suitable for use with herbicides and plant growth regulators other than the cyclohexenones. In greenhouse trials, haloxyfop methyl and imazethapyr were formulated into tank mixes with no adjuvant, with OC, and with RTD-2. GR values were calculated by log prohibit regression from tests on ECHCG and SETVI. Spray volume was 187 L/ha at a pressure of 241 kPa.

TABLE VI

GR[1] Values for Haloxyfop methyl and Imazethapyr

| Herbicide | Adjuvant @ Rate | $GR_{50}$ | $GR_{80}$ |
|---|---|---|---|
| Imazethapyr | None | 0.091 | 0.138 |
| " | OC | 0.030 | 0.054 |
| " | RTD-2 | 0.007 | 0.024 |
| Haloxyfop methyl | None | 0.037 | 0.058 |
| " | OC | 0.024 | 0.034 |
| " | RTD-2 | 0.016 | 0.024 |

[1] Lower GR values represent better weed control.

RTD formulations were prepared with haloxyfop methyl and imazethapyr. No difficulty was experienced in preparing formulations of haloxyfop methyl due to its ease of solubility in the RTD base system. However imazethapyr is difficultly soluble in most organic solvents and hence was induced to dissolve by preparing ion-pair salts through reaction of a fatty amine, and by the addition of methanol. Suitable formulations of imazethapyr, in weight percent, are as follows:

TABLE VII

|  | Formulation 1 | Formulation 2 |
|---|---|---|
| Imazethapyr | 5.0 | 5.0 |
| oleylamine | 5.0 | — |
| Ethosmeen ® S/12[1] | — | 6.0 |
| methanol | 10.0 | 10.0 |
| RTD-2 base | 80.0 | 79.0 |

[1]Ethomeen ® S/12 is a bis(2-hydroxyethyl)soyamine available from Akzo Chemie America, Armak Chemicals 300 S. Wacker Drive, Chicago, Ill.

Both formulations were acceptable in emulsion testing, as were each of the other RTD formulations of the subject invention. All rapidly dispersed in water containing moderate amounts of hardness, and remained dispersed for a period in excess of that necessary for application in the field. In the claims which follow, the term "herbicide" should be taken to include other agriculturally active chemicals such as plant growth regulators and the like.

I claim:

1. A ready-to-dilute herbicide composition comprising:
    (a) one or more herbicides selected from the group consisting of diphenylether herbicides, phenoxyphenoxy herbicides, imidazoline herbicides and cyclohexanone herbicides, in an amount of from 10 to about 250 g/L based upon the volume of the total composition;
    (b) an effective amount of a surface active emulsifier component comprising:
        (i) a polyoxyalkylene nonionic surfactant having an HLB of from 10 to about 14, and
        (ii) an anionic surfactant selected from the group consisting of the dialkylmetalsulfosuccinates and the metal alkylaromatic sulfonates;
    (c) optionally from 0 to about 100 g/l of a second surface active component comprising a polyoxyalkylene nonionic surfactant having an HLB of less than 10; and
    (d) about 100 g/L or more of one or more lower alkanol esters of a fatty acid,
        wherein said composition retains in excess of about 70 percent of its herbicidal activity after storage at about 40° C. for one year.

2. The composition of claim 1 wherein said emulsifier component (b)(ii) is selected from the group consisting of the dialkylalkalisulfosuccinates and the alkali and alkaline earth benzenesulfonates.

3. The composition of claim 1 wherein said nonionic surfactant (b)(i) is a polyoxyalkylated alkylphenol or polyoxyalkylated aliphatic alcohol having an HLB of about 12.

4. The composition of claim 1 wherein said polyoxyalkylene nonionic surfactant (c) is present in an amount of from 20 to about 80 g/L.

5. The composition of claim 1 wherein said herbicide is a cyclohexenone herbicide present in an amount of from 20 to about 200 g/liter; wherein component (b)(i) is a POE (8) nonylphenol; wherein component (b)(ii) is a dialkylsodium sulfosuccinate; wherein component (b) is present in an amount of from 10 to about 50 g/liter; wherein component (c) is a fatty alcohol initiated polyoxyethylenepolyoxypropylene block surfactant present in an amount of from 20 to about 100 g/liter; and wherein component (d) is a mixture of the methyesters of $C_{10}$–$C_{20}$ fatty acids.

6. The composition of claim 5 wherein said cyclohexenone herbicide is present in an amount of from 40 to about 150 g/L and wherein said methyl esters are predominantly the methylesters of palmitic and oleic acids.

7. The composition of claim 1 further comprising a minor portion of a paraffinic or aromatic solvent.

8. The composition of claim 5 further comprising a minor portion of a paraffinic hydrocarbon component.

* * * * *